United States Patent [19]

Haddon et al.

[11] 4,249,013
[45] Feb. 3, 1981

[54] CONJUGATIVELY LINKED TETRATHIAFULVALENES AND METHOD FOR PREPARATION THEREOF

[75] Inventors: Robert C. Haddon, Summit; Martin L. Kaplan, Morris Plains; Fred Wudl, Chester, all of N.J.

[73] Assignee: Bell Telephone Laboratories, Incorporated, Murray Hill, N.J.

[21] Appl. No.: 6,655

[22] Filed: Jan. 26, 1979

Related U.S. Application Data

[62] Division of Ser. No. 887,882, Mar. 20, 1978, abandoned.

[51] Int. Cl.³ .......................................... C07D 339/06
[52] U.S. Cl. ..................................... 549/35; 252/408; 350/357; 252/299
[58] Field of Search ...................... 260/327 M; 549/35

[56] References Cited

U.S. PATENT DOCUMENTS

| | | | |
|---|---|---|---|
| 3,451,741 | 6/1969 | Manos | 350/357 |
| 3,453,038 | 7/1969 | Kissa et al. | 350/160 |
| 3,779,814 | 12/1973 | Miles et al. | 549/35 |
| 3,806,229 | 4/1974 | Schoot et al. | 260/160 LC |
| 3,941,809 | 3/1976 | Kaplan et al. | 549/35 |
| 4,036,648 | 7/1977 | Engler et al. | 96/90 R |
| 4,090,782 | 5/1978 | Bredfeldt et al. | 350/357 |

OTHER PUBLICATIONS

Calas et al., Mol. Cryst. Liq. Cryst. vol. 32, pp. 151–153 (1976).
Kaplan et al., Chemical Abstracts, vol. 87, abst. 201387b (1977) (abst. of J. Chem. Soc. Commun. 1977 (11) pp. 388–389).
Livingston, Chemistry vol. 38, p. 5 (Technique in the Chem. Lab. IX, "I didn't know it was loaded!") (May 1965).
Bergmann, The Chemistry of Acetylene and Related Compounds, frontispage and page 80, Interscience Publishers, Inc., N. Y. (1948).
*Ueno et al., Chemistry Letters (Japan), pp. 603–606 (1975).
Calas et al., Comptes Rendus, Series C., vol. 280, pp. 901 to 903, Apr. 7, 1975.

*Primary Examiner*—John D. Randolph
*Attorney, Agent, or Firm*—Peter V. D. Wilde; Edward M. Fink

[57] ABSTRACT

A technique is described for the preparation of novel conjugatively linked tetrathiafulvalenes. The resultant molecule includes two donor moieties which allow the preparation of charge transfer complexes with a band structure higher than the quasi one dimensional structure indigenous to presently known electrically conducting organic complexes.

2 Claims, 1 Drawing Figure

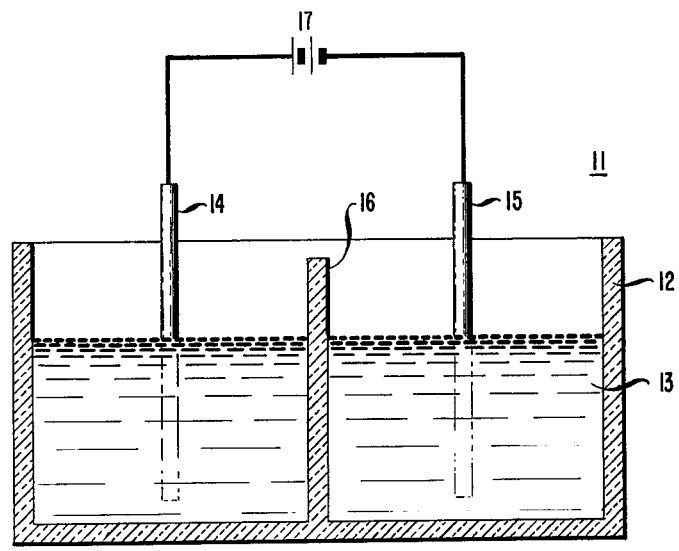

CONJUGATIVELY LINKED TETRATHIAFULVALENES AND METHOD FOR PREPARATION THEREOF

This is a division of application Ser. No. 887,882 filed Mar. 20, 1978, now abandoned.

This invention relates to a method for the preparation of conjugatively linked tetrathiafulvalenes, to the compositions so produced and to devices incorporating said compositions.

Recently, there has been a birth of interest in a class of compounds commonly referred to as fulvalenes. These compounds and, particularly, that identified as 1,4,5,8-tetrahydro-1,4,5,8-tetrathiafulvalene of the formula

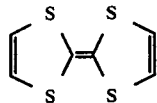

have been found to form stable radical cation salts which evidence high d-c conductivity, so suggesting their use as solid state organic conductors and particularly in electrochromic devices. The organic conductors reported heretofore are one-dimensional structures which have been found to undergo metal-to-insulator transitions while cooling. Accordingly, workers in the art have focused their interest upon the development of charge transfer complexes in the tetrathiafulvalene system which evidence a band structure higher than the quasi one-dimensional structure characteristic of all known electrically conducting organic complexes.

In accordance with the present invention, this end is attained by means of a novel conjugatively linked tetrathiafulvalene structure wherein a linking molecule couples tetrathiafulvalene molecules and disrupts the quasi one-dimensional band structure which is characteristic of tetrathiafulvalene charge transfer complexes.

The composition described herein is of the general formula

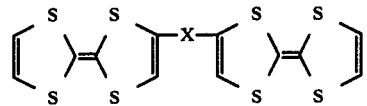

wherein X is selected from the groups consisting of $C_6H_4$, $(C_2)_y$, and $(C_2H_2)_z$, y and z being integers from 1-2.

The compositions described herein are of particular interest for use in an electrochromic device wherein salts thereof are relied upon for display characteristics.

The invention will be more readily understood by reference to the following detailed description taken in conjunction with the accompanying drawing wherein:

The Figure is a front elevational view in cross-section of a typical device in accordance with the invention.

With reference now more particularly to the Figure, there is shown an electrochromic device 11 including a cell 12 having disposed therein a mixture of a solution of tetrathiafulvalene and supporting electrolyte 13, a pair of electrodes 14 and 15 immersed in said mixture, a salt bridge 16 separating the electrodes and means 17 for impressing a difference of potential across said electrodes.

Electrodes chosen for use in the described device may be selected from among any of the known conductors, the prime requirement being that at least one side thereof is transparent. An electrode found to be of particular interest for this purpose is a tin oxide coated glass. Electrolytes employed are typically selected from among the alkyl ammonium salts. Tetrabutyl ammonium fluoborate is particularly well suited for this purpose.

In the operation of the device, electrode 14, which is transparent, is connected to the positive side of a source of direct current and electrode 15 connected to the negative side thereof. Following, a difference of potential is impressed across the electrodes, so causing deposition of said tetrathiafulvalene (purple in color) upon the transparent electrode from the orange colored tetrathiafulvalene solution. The device is therefore suitable for electrochromic applications.

A general outline of a procedure for preparing the novel tetrathiafulvalenes of the invention is set forth below. For purposes of exposition, this description is in terms of a composition wherein X in the formulation above represents a phenylene radical. It will, however, be understood that X may also represent the other groups noted above.

The first step in preparing tetrathiafulvalenes in accordance with the present invention includes reacting a 1,4-bis (haloacetyl) benzene in solution with a refluxing solution of a monovalent salt (Z in formula is a cation) of dialkyldithiocarbamic acid in solution to yield a dithiocarbamate as shown in Equation (1) below:

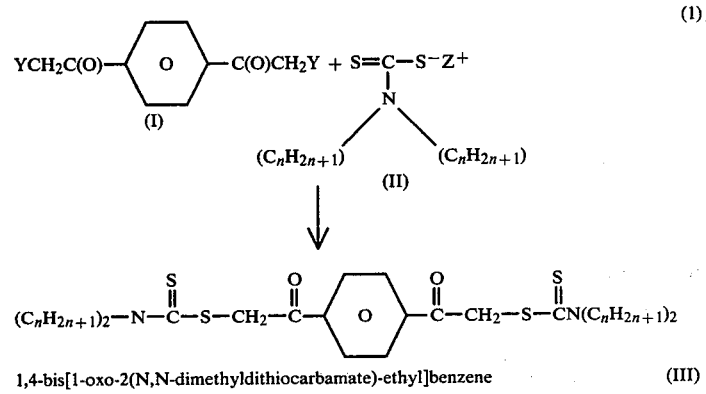

1,4-bis[1-oxo-2(N,N-dimethyldithiocarbamate)-ethyl]benzene     (III)

Then, refluxing is continued for a time period of the order of 20 hours and the mixture filtered to obtain a solid product which is washed and recrystallized. Next, the resultant compound (III) is reacted with anhydrous fluoboric acid in stoichiometric amounts to yield a cyclicized fluoborate derivative of the type shown in Equation (2) below:

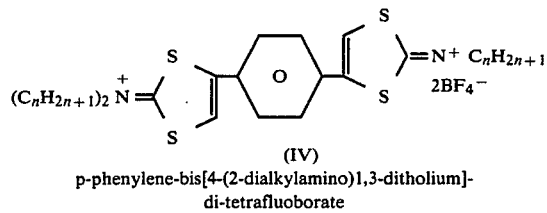

(IV)
p-phenylene-bis[4-(2-dialkylamino)1,3-ditholium]-di-tetrafluoborate

This reaction may conveniently be effected at the boiling point of the mixture over a time period ranging up to about 5 minutes. The resultant homogeneous solution is then removed from the heat and permitted to stand overnight at room temperature. The desired tetrafluoborate is then recovered by filtration and dried.

Following, the bis-ditholium salt, (IV), is subjected to reduction (in the presence of any polar solvent). Reducing agents suitable for use in effecting this reaction are selected from among the metal borohydrides, the alkali metal borohydrides being particularly suited for this purpose. Sodium borohydride (NaBH$_4$) has proven most effective. This reduction must be effected at temperatures less than 15° C. due to the exothermic nature of the reaction, a large excess of the borohydride, well beyond stoichiometry, being employed. The reduction reaction is shown in Equation (3) below:

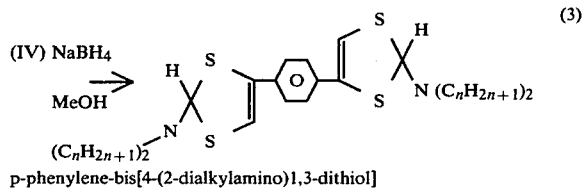

p-phenylene-bis[4-(2-dialkylamino)1,3-dithiol]

Finally, the resultant bis-dithiol is subjected to deamination by dropwise addition of fluoboric acid in solution and the product isolated by filtration, washed and dried, a bis-dithiolium salt being obtained as shown in Equation (4) below:

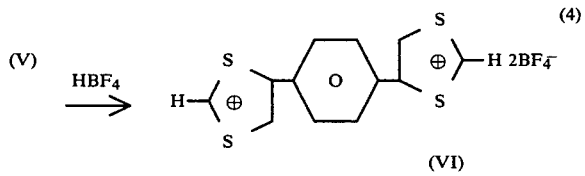

The desired p-phenylenebistetrathiafulvalene is then obtained by reacting the bis-dithiolium salt (VI), with sulfolane at room temperature in the presence of triethylamine in accordance with Equation (5).

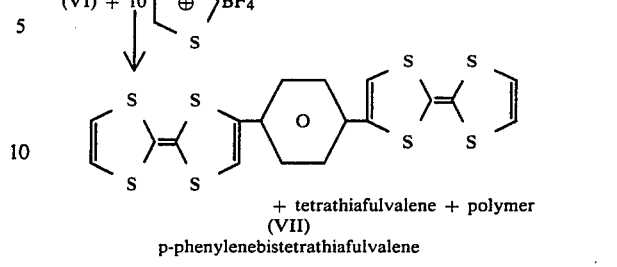

+ tetrathiafulvalene + polymer
(VII)
p-phenylenebistetrathiafulvalene

An example of the present invention is set forth below. It will be understood by those skilled in the art that the example is not restrictive in nature.

EXAMPLE

A slurry comprising 16 grams (0.05 mole) of 1,4-bis(-bromoacetyl) benzene in 100 ml of acetone was added to a refluxing solution of 19.7 grams (0.11 mole) of the sodium salt of dimethyldithiocarbamic acid. Refluxing was continued for a period of four hours. Then, the refluxed mixture was stirred for 16 hours and refluxed an additional 4 hours. Next, the mixture was filtered and the solid washed with hot water. The product was recrystallized from hot 1,2-dichloroethane to yield 13 grams of near white crystals melting at 214°–215° C. The nmr spectrum in CDCl$_3$(TMS) exhibited a broad doublet at tau 6.49, singlet at 5.13 and singlet at 1.80. The resultant product was 1,4-bis[1-oxo-2(N,N-dimethyldithiocarbamate)-ethyl]benzene.

Then, 4.0 grams (0.01 mole) of the bis-dithiocarbamate were added to a solution containing 8.8 grams of 40% aqueous fluoboric acid in acetic anhydride. The resultant mixture was stirred ahd heated at the boiling point for approximately 3 minutes, so resulting in a homogeneous solution which was removed from the heat and permitted to stand at room temperature. After standing overnight, a solid formed which was then removed by filtration, washed with acetic anhydride and dried under nitrogen. The product resulting was a tan substance (5.06 grams) melting above 300° C. which was identified as p-phenylene-bis[4-(2-dimethylamino)1,3-ditholium]ditetrafluoborate. The nmr spectrum thereof in trifluoroacetic acid (TMS) exhibited a doublet at tau 6.3 and singlets at 2.37 and 2.18.

Next, 760 mg. (20 mmol) of sodium borohydride were added to a slurry of 540 mg. (1 mmol) of the ditetrafluoborate and 25 ml. of ethanol at 0° C. Stirring was initiated at that temperature and continued for 30 minutes. 75 ml. of water was then added to the mixture and a flocculent yellow precipitate resulted. The precipitate was collected by filtration, washed with water and dried under nitrogen. The yield was 0.37 gram (100%) and the product melted at a temperature ranging from 136.5° to 137.0° C. Its nmr spectrum in deuterochloroform (TMS) showed four singlets at taus 7.72, 3.70, 3.52 and 2.57. The product was identified as p-phenylene-bis[4-dimethylamino)1,3-dithiol].

A solution comprising 3.52 grams of 40% fluoboric acid in acetic anhydride was then added dropwise at 0° C. to a slurry comprising 0.74 gram of the p-phenylene-bis[4-(2-dimethylamino)1,3-dithiol] in 20 ml. of acetic anhydride. The mixture turned rust colored and was stirred at 0° C. for 10 minutes and then at room temperature for 45 minutes. The product was isolated by filtration, washed with acetic anhydride and ether. The dried product weighed 0.78 grams (86%) and evidenced an nmr spectrum in nitromethane (TMS) which showed doublets at taus 1.37 and 0.45 and a singlet at 1.73. The product was identified as p-phenylene-bis-[4-(1,3-dithiolium)]ditetrafluoborate.

The final step in the process involved adding 3.8 grams of 1,3-dithioliumtetrafluoborate to a solution comprising 454 mg. of the ditetrafluoborate in 50 ml. of sulfolane at room temperature. Six grams of triethylamine was then added with rapid stirring. Stirring was continued for 10 minutes under argon at which time 800 ml. of deaerated water was added, so yielding an orange precipitate which was washed with water and then dried. The product was extracted in a Soxhlet apparatus with hexane. The material remaining in the Soxhlet thimble was then extracted with carbon disulfide until the extracts were colorless. The concentrated carbon disulfide extracts were chromatographed on six 2 mm. silica gel thick layer plates (20 cm.×20 cm.) with carbon disulfide. The orange bands were collected, extracted with carbon disulfide and the orange solutions concentrated to yield 100 mg. (21%) of p-phenyleneditetrathiafulvalene. The melting point of the product ranged from 241.9° to 242.4° C. The ultraviolet visible spectrum in p-dioxane showed maxima ($\lambda$) at 296 (SH) nm (19,800), 310 (21,700), 320 (21,600) and 440 (4020). The nmr spectrum was three singlets at taus 3.80, 3.63 and 2.75 in the ratio of 2:1:2. The mass spectrum showed a molecular ion at m/e 482.

A salt of p-phenylenebistetrathiafulvalene was prepared by mixing solutions of the tetrathiafulvalene and tetracyanoquinodimethane in hot benzonitrile. The black solid which formed was collected, washed with acetonitrile and ether and then dried. The solid analyzed at 1:1 salt and its compressed pellet room temperature resistivity was about 10 (ohm-cm)$^{-1}$.

What is claimed is:
1. p-phenylenebistetrathiafulvalene.
2. Electrically conducting salt formed by reaction of p-phenylenebistetrathiafulvalene and tetracyanoquinodimethane.